US00PP13870P39

(12) United States Plant Patent
Bregeon

(10) Patent No.: US PP13,870 P3
(45) Date of Patent: Jun. 10, 2003

(54) *PINUS NIGRA* PLANT NAMED 'MARIE BREGEON'

(76) Inventor: Henri Bregeon, Chemin d'Arzillier 13, 1020 Renens (CH)

( * ) Notice: Subject to any disclaimer, the term of this patent is extended or adjusted under 35 U.S.C. 154(b) by 2 days.

(21) Appl. No.: 09/905,966

(22) Filed: Jul. 17, 2001

(65) Prior Publication Data

US 2003/0019000 P1 Jan. 23, 2003

(51) Int. Cl.[7] ..... A01H 7/00
(52) U.S. Cl. ..... Plt./213
(58) Field of Search ..... Plt./213

(56) References Cited

PUBLICATIONS

UPOV ROM GTITM Computer Database, GTI JOUVE Retrieval Software, citation for 'Marie Bregon' 2002/02.*

* cited by examiner

*Primary Examiner*—Bruce R. Campell
*Assistant Examiner*—W C Haas
(74) *Attorney, Agent, or Firm*—Foley & Lardner

(57) ABSTRACT

A distinct Pinus plant named 'Marie Bregeon' characterized by natural round plant shape without trimming; light green foliage; spiraling needles; annual growth rate between 5 and 9 cm; cylindrical and gray buds in winter without resin and with a pointy tip; cylindrical and light brown buds in spring without resin; and light gray stipule around the needles, visible in the winter.

2 Drawing Sheets

LATIN NAME OF THE GENUS AND SPECIES OF THE PLANT CLAIMED

*Pinus nigra.*

VARIETY DENOMINATION

Marie Bregeon.

BACKGROUND OF THE INVENTION

The present invention relates to a new and distinct cultivar of Pinus plant, botanically known as *Pinus l.,* and hereinafter referred to by the name 'Marie Bregeon'.

The new cultivar was originated from a cross made in a controlled breeding program in Renens VD, Switzerland in 1986. The female parent in *Pinus nigra* '107' an unprotected non-commercial variety owned by the applicant. The male parent is *Pinus densiflora* '32' (unpatented) a non-commercial variety owned by the applicant. 'Marie Bregeon' was discovered and selected by the inventor, Henri Bregeron, as a garden plant within the progeny of the stated cross in a controlled environment in Renens, VD, Switzerland.

'Marie Bregeon' is a product of a planned breeding program conducted by the Inventor and selected in a cultivated environment in Renens, VD, Switzerland. Asexual reproduction of the new cultivar by vegetative reproduction, grafting was first performed in Feb., 1990, in Renens VD, Switzerland and has demonstrated that the combination of characteristics as herein disclosed for the new cultivar are firmly fixed and reproduce true to type in successive generations of asexual reproduction.

BRIEF DESCRIPTION OF THE INVENTION

The following traits have been repeatedly observed and are determined to be basic characteristics of 'Marie Bregeon' which in combination distinguish this Pinus as a new and distinct cultivar:

1. Natural round plant shape without trimming;

2. Light green foliage;
3. Spiraling needles;
4. Annual growth rate between 5 and 9 cm;
5. Cylindrical and gray buds in winter without resin and with a pointy tip;
6. Cylindrical and light brown buds in spring without resin;
7. Light gray stipule around the needles, visible in the winter.

'Marie Bregeon' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Renens VD, Switzerland under conditions which closely approximate those generally used in commercial practice.

Of the many commercial cultivars known to the present inventor, the most similar in comparison to *Pinus nigra* 'Marie Bregeon' are cultivars 'Pierrick Bregeon' and 'Baelle Bregeon', both varieties are unpatented and owned by the applicant. The most important unique and distinct characteristics are the following: This variety is as a whole a very unique and distinct *Pinus Nigra* cultivar. The plant shape of *Pinus nigra* 'Marie Bregeon' is rounder than the plant shape of both Pinus 'Gaelle Bregeon' and Pinus 'Pierrick Bregeon'. The foliage color of 'Marie Bregeon' is lighter green than the foilage color of both Pinus 'Gaelle Bregeon' and Pinus 'Pierrick Bregeon'. The mature needles of *Pinus nigra* 'Marie Bregeon' are more spirally formed than the needles of Pinus 'Gaelle Bregeon' and Pinus 'Pierrick Bregeon'. The stipule around a 'Marie Bregeon' needle is light gray, contrary to the stipules around the needles of Pinus 'Gaelle Bregeon' and Pinus 'Pierrick Bregeon' which are brown. 'Marie Bregeon' has a slower growth rate than 'Pierrick Bregeon'. Bracts covering the beginning of the needles of 'Marie Bregeon' are up to 10 mm long and very visible, contrary to the bracts of 'Gaelle Bregeon' which are less than 1 mm long and are hardly visible. 'Marie Bregeon' has almost no resin production, contrary to 'Gaelle Bregeon' and 'Pierrick Bregeon' which have a light resin production. The viability of the needles of 'Marie Bregeon' is three to four years contrary to the needles of 'Pierrick Bregeon' and 'Gaelle Bregeon' which have a viability of two to three years.

BRIEF DESCRIPTION OF THE DRAWING

The accompanying photographic illustrations show a three year old plant of 'Marie Bregeon' with colors being as true as possible with illustrations of this type.

The first drawing shows a three year old plant of 'Marie Bregeon'.

The second drawing shows a three year old plant of 'Marie Bregeon' with a 3 year old plant of 'Gaelle Bregeon'.

DETAILED BOTANICAL DESCRIPTION

The following observations, measurements and values describe the new cultivar at 36 months, as grown in Renens VD, Switzerland, in Jun. 2001, under conditions which closely approximate those generally used in commercial practice. 'Marie Bregeon' can be propagated by cuttings but for commercial purposes this variety is usually grafted. Both propagation methods are done in a standard greenhouse in temperatures between 4 and 10 degrees Celsius.

The described plants were grown outdoor in temperatures between −15 degrees Celsius and +35 degrees Celsius. No artificial lighting or photoperiodic treatments are conducted. Highest temperature resistance is +45 degrees Celsius, lowest −30 degrees Celsius. The fertilizer Osmocote is added. In event of propagation by cuttings a cutting, prepared with cutting medium, is planted in soil in the winter. The humidity is kept between 90 and 100 percent to prevent dry out of the cutting. At the end of May the plant should have produced roots. However, experiences with this type of propagation showed a success rate of only 2 per 1000 cuttings. Therefore, grafting is recommended. In event of grafting: from the start of grafting it takes 9 months to produce a commercial plant. The trunk of *Pinus sylvestris* is used as rootstock for grafting. Grafting is initiated in the winter when the plants are in rest and a temperature of about 8 degrees Celsius in a greenhouse. At the end of May the top of the *Pinus sylvestris* is removed and in early July the plant is moved outdoor. The plants used for this description therefore have the trunk of a *Pinus sylvestris* and the head of a 'Marie Bregeon'. Grafting for bigger size plants are grafted on *Pinus nigra*.

Color references are made to The Royal Horticultural Society Colour Chart (R.H.S.), except where general colors of ordinary significance are used. Color values were taken under daylight conditions at approximately noon in Rijswijk, The Netherlands.

Origin: Renens, VD, Switzerland.
Parentage:
- *Male parent.*—*Pinus nigra* '107'.
- *Female parent.*—*Pinus densiflora* '32'.

Propagation:
- *Type cutting.*—Cuttings or grafting on a rootstock.

Plant:
- *General appearance and form.*—Round.
- *Height.*—Average 35 cm.
- *Width.*—30 cm.
- *Growth habit.*—Round.
- *Winter hardiness.*—Very good, minimum temperature tolerance is minus 30 degrees Celsius.
- *Plant vigor.*—Growth rate is 5–9 cm per year.
- *Trunk diameter.*—1.8 cm at bottom.

Twigs/branches:
- *Branching frequency.*—Internodes are very close to each other with up to five twigs around the same point on a branch.
- *Length.*—16 cm.
- *Diameter.*—Up to 14 mm.
- *Spread.*—Up to 17 cm.
- *Amount.*—Up to 6 twigs per branch and about 6 to 8 branches on trunk.
- *Color.*—RHS 165 C.

Foliage:
- *Primary needles.*—Color: RHS 137C. Length: Up to 9–10 cm. Viability: Needles last 3 to 4 years.
- *Secondary needles.*—Color: Grayish green, RHS 192 B, with grayed white, RHS 165 D, and grayed orange. Length: Up to 10 mm. Viability: Unknown.

Bracts:
- *Amount.*—1 which is very visible.
- *Color.*—RHS 199 A and RHS 200 D.

Roots:
- *Time to initiate roots.*—Four months when propagated by cuttings.
- *Time to develop roots.*—Five months at temperatures starting between 8 to 10 degrees that gradually increase.
- *Rooting habit.*—Freely branching.

Seeds: None observed.
Disease resistance/susceptibility: 'Marie Bregeon' has a high resistance against stresses and diseases, no diseases have been observed so far.

I claim:

1. A new and distinct Pinus plant named 'Marie Bregeon', substantially as illustrated and described herein.

* * * * *

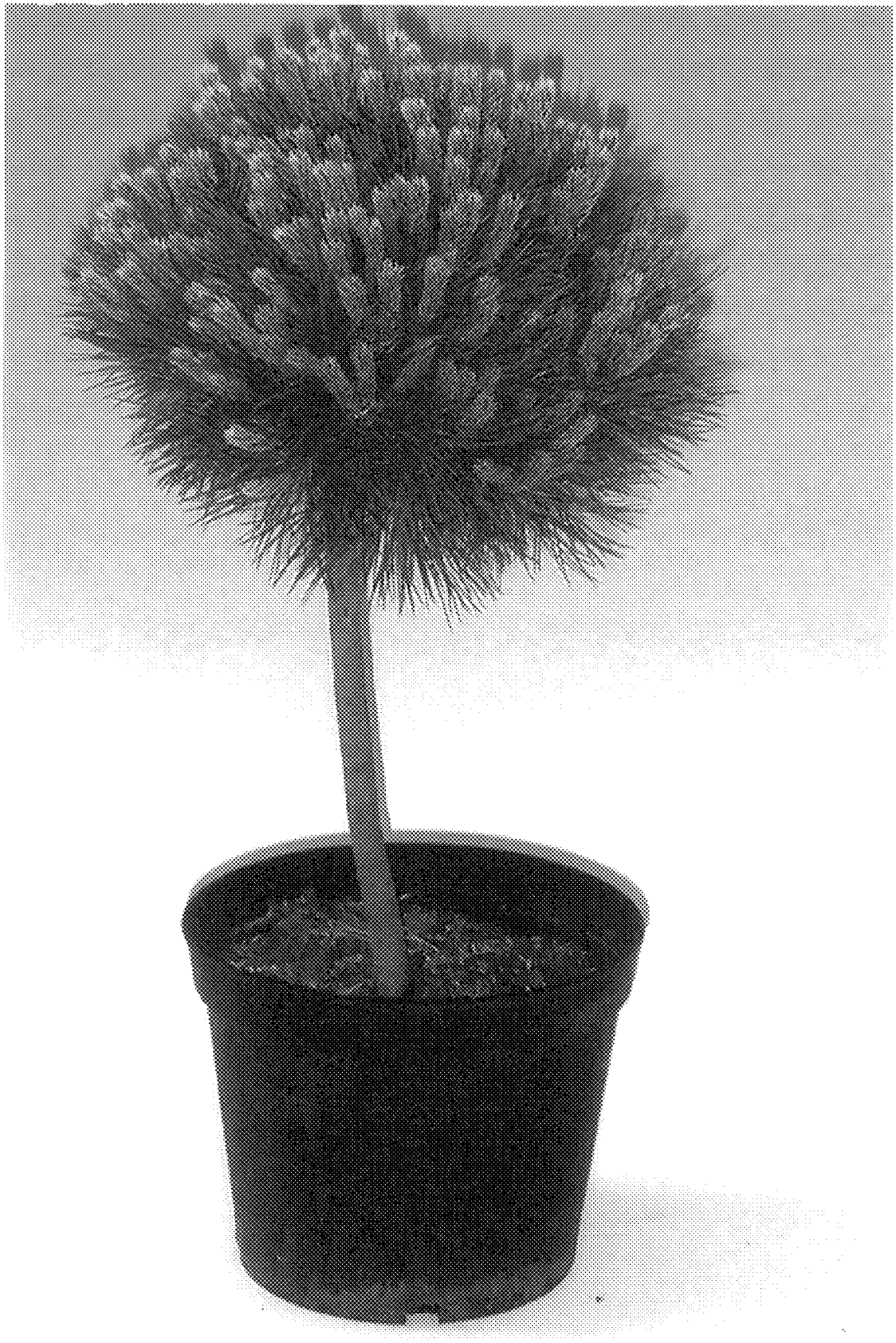

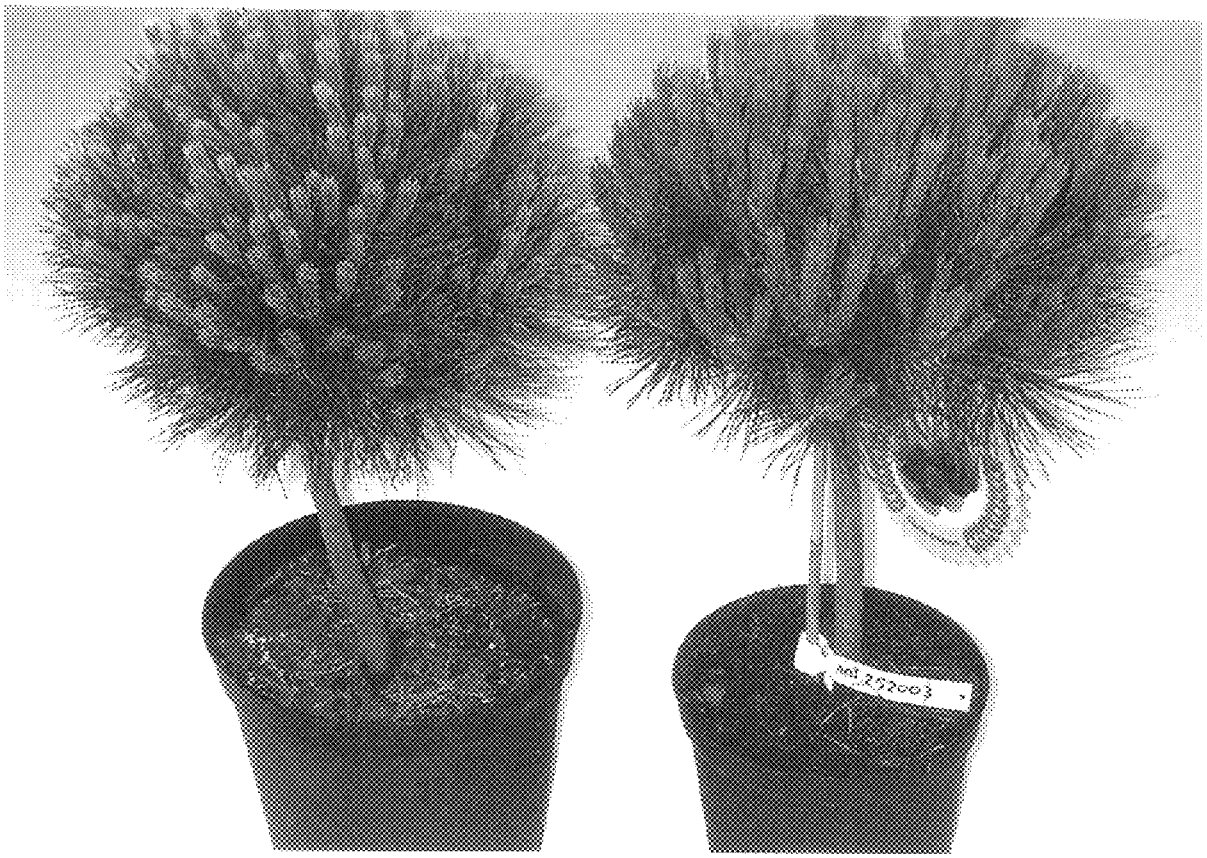
ad 252003